(12) United States Patent
Carpenter et al.

(10) Patent No.: US 8,234,076 B2
(45) Date of Patent: Jul. 31, 2012

(54) ABNORMAL OUTPUT DETECTION SYSTEM FOR A BIOSENSOR

(75) Inventors: Scott Carpenter, Pendleton, IN (US); Christine D. Nelson, Edwardsburg, MI (US); Huan-Ping Wu, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 715 days.

(21) Appl. No.: 12/253,440

(22) Filed: Oct. 17, 2008

(65) Prior Publication Data

US 2009/0099787 A1    Apr. 16, 2009

Related U.S. Application Data

(63) Continuation of application No. PCT/US2007/068320, filed on May 7, 2007.

(60) Provisional application No. 60/746,771, filed on May 8, 2006.

(51) Int. Cl.
*G01N 33/48* (2006.01)
*G01N 31/00* (2006.01)
*C12Q 1/00* (2006.01)

(52) U.S. Cl. ................. 702/19; 702/22; 435/4

(58) Field of Classification Search .................. None
See application file for complete search history.

(56) References Cited

U.S. PATENT DOCUMENTS

| | | |
|---|---|---|
| 4,431,004 A | 2/1984 | Bessman et al. |
| 4,750,496 A | 6/1988 | Reinhart et al. |
| 5,243,516 A | 9/1993 | White |
| 5,366,609 A | 11/1994 | White et al. |
| 5,395,504 A | 3/1995 | Saurer et al. |
| 5,508,171 A | 4/1996 | Walling et al. |
| 5,582,697 A | 12/1996 | Ikeda et al. |
| 5,620,579 A | 4/1997 | Genshaw et al. |
| 5,653,863 A | 8/1997 | Genshaw et al. |
| 6,120,676 A | 9/2000 | Heller et al. |
| 6,153,069 A | 11/2000 | Pottgen et al. |
| 6,391,645 B1 | 5/2002 | Huang et al. |
| 6,413,411 B1 | 7/2002 | Pottgen et al. |
| 6,531,040 B2 | 3/2003 | Musho et al. |
| 6,576,117 B1 | 6/2003 | Iketaki et al. |
| 2003/0235817 A1* | 12/2003 | Bartkowiak et al. ............. 435/5 |

(Continued)

FOREIGN PATENT DOCUMENTS

WO     WO 9614026     10/1995

OTHER PUBLICATIONS

Bakker et al. (SIAM Review, vol. 45, No. 2, p. 327-344, 2003).*

(Continued)

*Primary Examiner* — Russell S Negin
(74) *Attorney, Agent, or Firm* — Blanchard & Associates (57) ABSTRACT

A biosensor has an abnormal output detection system that determines whether an output signal from the redox reaction of an analyte has a normal or abnormal shape or configuration. The abnormal output detection system improves the accuracy and precision of the biosensor in determining whether an output signal has a shape or configuration that may not provide an accurate and/or precise analysis of a biological fluid. The biosensor generates an output signal in response to the redox reaction of the analyte. The biosensor normalizes the output signal and compares the normalized output signal with one or more control limits. The biosensor may generate an error signal when the normalized output signal is not within the control limits.

28 Claims, 3 Drawing Sheets

U.S. PATENT DOCUMENTS

2004/0260511 A1  12/2004  Burke et al.
2007/0231914 A1  10/2007  Deng et al.
2008/0173552 A1   7/2008  Wu et al.
2008/0179197 A1   7/2008  Wu

OTHER PUBLICATIONS

Aussedat et al. (Biosensors & Bioelectronics vol. 12. No. 11, pp. 1061-1071, 1997).*

EPO, "Search Report and Written Opinion for PCT/US2007/068320", Oct. 19, 2007, Publisher: International Search Authority.

Bard, et al., "Electrochemical Methods Fundamentals and Applications", 1980, pp. 236.

Gunasingham, et al., "Pulsed amperometric detection of glucose using a mediated enzyme electrode", "Journal of Electroanalytical Chemisty", 1990, pp. 349-362, vol. 287, No. 2.

* cited by examiner

ABNORMAL OUTPUT DETECTION SYSTEM FOR A BIOSENSOR

REFERENCE TO RELATED APPLICATIONS

This application is a continuation of PCT/US2007/68320 entitled "Abnormal Output Detection System for a Biosensor" filed May 7, 2007, which was published in English and claimed the benefit of U.S. Provisional Application No. 60/746,771 entitled "Abnormal Output Detection System for a Biosensor" filed May 8, 2006, which are incorporated by reference in their entirety.

BACKGROUND

Biosensors usually provide an analysis of a biological fluid, such as whole blood, urine, or saliva. Typically, a biosensor analyzes a sample of the biological fluid to determine the concentration of one or more analytes, such as glucose, uric acid, lactate, cholesterol, or bilirubin, in the biological fluid. The analysis is useful in the diagnosis and treatment of physiological abnormalities. For example, a diabetic individual may use a biosensor to determine the glucose level in blood for adjustments to diet and/or medication.

A biosensor may provide an abnormal output during the analysis of the biological fluid. The abnormal output may be in response to an error during the analysis of the biological fluid. The error may be from one or more factors such as the physical characteristics of the sample, the environmental aspects of the sample, the operating conditions of the biosensor, interfering substances, and the like. Physical characteristics of the sample include the hematocrit level and the like. Environmental aspects of the sample include temperature and the like. Operating conditions of the biosensor include underfill conditions when the sample size is not large enough, slow-filling of the sample, intermittent electrical contact between the sample and one or more electrodes in the biosensor, and the like. Interfering substances include ascorbic acid, acetaminophen, and the like. There may be other factors and/or a combination of factors that cause the error and/or abnormal output.

Biosensors may be implemented using bench-top, portable, and like devices. The portable devices may be hand-held. Biosensors may be designed to analyze one or more analytes and may use different volumes of biological fluids. Some biosensors may analyze a single drop of whole blood, such as from 0.25-15 microliters ($\mu$L) in volume. Examples of portable measuring devices include the ASCENSIA BREEZE® and ELITE® meters of Bayer Corporation; the PRECISION® biosensors available from Abbott in Abbott Park, Ill.; ACCUCHECK® biosensors available from Roche in Indianapolis, Ind.; and ONETOUCH ULTRA® biosensors available from Lifescan in Milpitas, Calif. Examples of bench-top measuring devices include the BAS 100B Analyzer available from BAS Instruments in West Lafayette, Ind.; the CH Instruments' Electrochemical Workstation available from CH Instruments in Austin, Tex.; the Cypress Electrochemical Workstation available from Cypress Systems in Lawrence, Kans.; and the EG&G Electrochemical Instrument available from Princeton Research Instruments in Princeton, N.J.

Biosensors usually measure an electrical signal to determine the analyte concentration in a sample of the biological fluid. The analyte typically undergoes an oxidation/reduction or redox reaction when an input signal is applied to the sample. An enzyme or similar species may be added to the sample to enhance the redox reaction. The input signal usually is an electrical signal, such as a current or potential. The redox reaction generates an output signal in response to the input signal. The output signal usually is an electrical signal, such as a current or potential, which may be measured and correlated with the concentration of the analyte in the biological fluid.

Many biosensors have a measuring device and a sensor strip. A sample of the biological fluid is introduced into a sample chamber in the sensor strip. The sensor strip is placed in the measuring device for analysis. The measuring device usually has electrical contacts that connect with electrical conductors in the sensor strip. The electrical conductors typically connect to working, counter, and/or other electrodes that extend into a sample chamber. The measuring device applies the input signal through the electrical contacts to the electrical conductors in the sensor strip. The electrical conductors convey the input signal through the electrodes into a sample deposited in the sample chamber. The redox reaction of the analyte generates an output signal in response to the input signal. The measuring device determines the analyte concentration in response to the output signal.

The sensor strip may include reagents that react with the analyte in the sample of biological fluid. The reagents may include an ionizing agent for facilitating the redox of the analyte, as well as mediators or other substances that assist in transferring electrons between the analyte and the conductor. The ionizing agent may be an analyte specific enzyme, such as glucose oxidase or glucose dehydrogenase, which catalyzes the oxidation of glucose in a whole blood sample. The reagents may include a binder that holds the enzyme and mediator together.

Many biosensors include one or more error detection systems to prevent or screen out analyses associated with an error. The concentration values obtained from an analysis with an error may be inaccurate. The ability to prevent or screen out these inaccurate analyses may increase the accuracy of the concentration values obtained. The error detection system may detect and compensate for an error such as a sample temperature that is different from a reference temperature. The error detection system may detect and stop the analysis of the biological fluid in response to an error such as an underfill condition.

Some biosensors have an error detection system that detects and compensates for the sample temperature. Such error detection systems typically compensate the analyte concentration for a particular reference temperature in response to the sample temperature. A number of biosensor systems compensate for temperature by changing the output signal prior to calculating the analyte concentration from a correlation equation. Other biosensor systems compensate for temperature by changing the analyte concentration calculated by the correlation equation. Biosensor systems having an error detection system for the sample temperature are described in U.S. Pat. Nos. 4,431,004; 4,750,496; 5,366,609; 5,395,504; 5,508,171; 6,391,645; and 6,576,117.

Some biosensors have an error detection system that detects whether an underfill condition exists. Such error detection systems typically prevent or screen out analyses associated with sample sizes that are of insufficient volume. A number of underfill detection systems have one or more indicator electrodes that detect the partial and/or complete filling of a sample chamber within a sensor strip. Some underfill detection systems have a third electrode in addition to counter and working electrodes used to apply an input signal to a sample of the biological fluid. Other underfill detection systems use a sub-element of the counter electrode to determine whether the sensor strip is underfilled. Biosensor systems having an error detection system for underfill conditions are described in U.S. Pat. Nos. 5,582,697 and 6,531,040.

While error detection systems balance various advantages and disadvantages, none are ideal. These systems usually are directed to detect and respond to a particular type of error. However, these systems typically do not assess or determine whether the output signal from the biosensor is a normal or abnormal response from the analysis of the biological fluid. Consequently, the biosensor may provide an inaccurate analysis when an error detection system does not detect an error. Additionally, the biosensor may provide an inaccurate analysis when an error detection system does not detect an error from a combination of factors that individually would not cause an error.

Accordingly, there is an ongoing need for improved biosensors, especially those that may provide increasingly accurate and/or precise detection of abnormal output signals from a biosensor. The systems, devices, and methods of the present invention overcome at least one of the disadvantages associated with conventional biosensors.

SUMMARY

The present invention provides a biosensor with an abnormal output detection system that determines whether an output signal from the redox reaction of an analyte has a normal or abnormal shape or configuration. An output signal with a normal shape or configuration may provide an accurate and/or precise analysis of a biological fluid. An output signal with an abnormal shape or configuration may not provide an accurate and/or precise analysis of a biological fluid. The biosensor generates an output signal in response to the redox reaction of the analyte. The biosensor measures and normalizes the output signal. The biosensor compares the normalized output signal with one or more control limits and generates an error signal when the normalized output signal is not within the control limits.

A method for detecting abnormal output in a biosensor includes normalizing an output signal from a redox reaction of analyte in a sample of a biological fluid, comparing a normalized output signal to at least one control limit, and generating an error signal when the normalized output signal is not within the at least one control limit. The method also may include determining a difference between at least one base output value and at least one measured output value of the output signal. The output signal may be responsive to a pulsed sequence, and the at least one base output value may be a measured output value of the output signal. The method also may include dividing at least one output value in a pulse of the output signal by the first output value in the pulse of the output signal, and the output signal may be responsive to a gated amperometry electrochemical system. The method also may include determining the at least one control limit from a statistical analysis of laboratory results.

The method may include generating the output signal in response to a pulsed sequence, and the pulsed sequence may comprise at least five pulses. The normalized current value of the fourth pulse, $R_4$, may be represented by the equation $$R_4 = \frac{i_{4,8}}{i_{4,1}},$$

where $i_{4,1}$ is the first current value in the fourth pulse and $i_{4,8}$ is the last current value in the fourth pulse. $R_4$ may be greater than or equal to 0.45, and $R_4$ may be less than or equal to 0.85.

The normalized current value of the fifth pulse, $R_5$, may be represented by the equation $$R_5 = \frac{i_{5,8}}{i_{5,1}},$$

where $i_{5,1}$ is the first current value in the fifth pulse and $i_{5,8}$ is the last current value in the fifth pulse. $R_5$ may be greater than or equal to 0.45, and $R_5$ may be less than or equal to 0.85. The ratio of the normalized current value of the fourth pulse to the normalized current value of the fifth pulse may be represented by the equation $$\text{Ratio} = \frac{i_{4,8} * i_{5,1}}{i_{4,1} * i_{5,8}},$$

where $i_{4,1}$ is the first current value in the fourth pulse, $i_{4,8}$ is the last current value in the fourth pulse, $i_{5,1}$ is the first current value in the fifth pulse, and $i_{5,8}$ is the last current value in the fifth pulse. The ratio of the normalized current value of the fourth pulse to the normalized current value of the fifth pulse may be greater than or equal to 0.75 and less than or equal to 1.2.

Another method for detecting abnormal output in a biosensor includes generating an output signal in response to a redox reaction of an analyte in a sample of a biological fluid, measuring the output signal, normalizing the output signal, comparing a normalized output signal to at least one control limit, and generating an error signal when the normalized output signal is not within the at least one control limit. The method may include applying an input signal to the sample of the biological fluid. The method may include measuring the output signal intermittently and at least eight current values may be measured in at least one pulse of the output signal. The method may include dividing at least one output value in a pulse of the output signal by the first output value in the pulse of the output signal. The method may include determining the at least one control limit from a statistical analysis of laboratory results.

The output signal may include at least five pulses where the normalized current value of the fourth pulse, $R_4$, is represented by the equation $$R_4 = \frac{i_{4,8}}{i_{4,1}},$$

where $i_{4,1}$ is the first current value in the fourth pulse and $i_{4,8}$ is the last current value in the fourth pulse. The normalized current value of the fifth pulse, $R_5$, may be represented by the equation $$R_5 = \frac{i_{5,8}}{i_{5,1}},$$

where $i_{5,1}$ is the first current value in the fifth pulse and $i_{5,8}$ is the last current value in the fifth pulse. The ratio of the normalized current value of the fourth pulse to the normalized current value of the fifth pulse may be represented by the equation $$\text{Ratio} = \frac{i_{4,8} * i_{5,1}}{i_{4,1} * i_{5,8}},$$

where $i_{4,1}$ is the first current value in the fourth pulse, $i_{4,8}$ is the last current value in the fourth pulse, $i_{5,1}$ is the first current value in the fifth pulse, and $i_{5,8}$ is the last current value in the fifth pulse.

The input signal may include a pulsed sequence, may be responsive to a gated amperometry electrochemical system, and/or may include a polling input signal and an assay input signal. The polling input signal may have a polling pulse width of less than about 300 ms, and the polling input signal may have a polling pulse interval of less than about 1 sec. The polling input signal may have a polling pulse width in the range of about 0.5 ms through about 75 ms and a polling pulse interval in the range of about 5 ms through about 300 ms. The assay input signal may have an assay pulse width of less than about 5 sec and an assay pulse interval of less than about 15 sec. The assay input signal also may have an assay pulse width in the range of about 0.1 sec through about 3 sec and an assay pulse interval in the range of about 0.2 sec through about 6 sec.

When the input signal comprises a polling input signal and an assay input signal, the method may include applying the polling input signal during a polling period, where the polling period is less than about 180 sec, and applying the assay input signal during an assay period, where the assay period is less than about 180 sec. When the input signal comprises a polling input signal and an assay input signal, the method may include applying the polling input signal during a polling period, where the polling period is in the range of about 0.1 sec through about 10 sec and applying the assay input signal during an assay period, where the assay period is in the range of about 1 sec through about 100 sec.

When the input signal comprises a polling input signal and an assay input signal, the method may include applying a polling input signal to the sample for about 1.25 sec, where the polling input signal has a polling pulse width of about 5-10 ms and a polling pulse interval of about 125 ms, and applying an assay input signal to the sample for about 7 sec, where the assay input signal has an assay pulse width of about 1 sec and an assay pulse interval of about 1.5 sec. The polling input signal may have a potential of about 400 mV, the assay input signal may have a first pulse with a potential of about 400 mV, and the assay input signal may have at least one other pulse with a potential of about 200 mV. The assay input signal may be applied when a polling output signal is greater than or equal to a polling threshold, and the polling threshold may be about 250 nA.

A biosensor, for determining an analyte concentration in a biological fluid, includes a sensor strip having a sample interface on a base, where the sample interface is adjacent to a reservoir formed by the base, a measuring device having a processor connected to a sensor interface, where the sensor interface has electrical communication with the sample interface, the processor normalizes an output signal from a redox reaction of an analyte in a sample of a biological fluid, the processor compares a normalized output signal to at least one control limit, and the processor generates an error signal when the normalized output signal is not within the at least one control limit. The processor may determine a difference between at least one base output value and at least one measured output value of the output signal and/or may divide at least one output value in a pulse of the output signal by the first output value in the pulse of the output signal. The at least one control limit may be predetermined from a statistical analysis of laboratory results.

The processor may apply an input signal to the sample of the biological fluid, where the input signal comprises a polling input signal and an assay input signal. The polling input signal may have a polling pulse width of less than about 300 ms and a polling pulse interval of less than about 1 sec. The assay input signal may have an assay pulse width of less than about 5 sec and an assay pulse interval of less than about 15 sec. The processor may apply the polling input signal during a polling period of less than about 180 sec and may apply the assay input signal during an assay period of less than about 180 sec. The processor may apply the polling input signal during a polling period in the range of about 0.1 sec through about 10 sec and may apply the assay input signal during an assay period in the range of about 1 sec through about 100 sec. The processor may apply a polling input signal to the sample for about 1.25 sec, where the polling input signal has a polling pulse width of about 5-10 ms, a polling pulse interval of about 125 ms, and a potential of about 400 mV. The processor may apply an assay input signal to the sample for about 7 sec, where the assay input signal has an assay pulse width of about 1 sec, an assay pulse interval of about 1.5 sec, a first pulse with a potential of about 400 mV, and at least one other pulse with a potential of about 200 mV. The processor may apply the assay input signal when a polling output signal is greater than or equal to a polling threshold of about 250 nA.

The output signal of the biosensor may include at least five pulses and the normalized current value of the fourth pulse, $R_4$, may be represented by the equation $$R_4 = \frac{i_{4,8}}{i_{4,1}},$$

where $i_{4,1}$ is the first current value in the fourth pulse and $i_{4,8}$ is the last current value in the fourth pulse. The normalized current value of the fifth pulse, $R_5$, may be represented by the equation $$R_5 = \frac{i_{5,8}}{i_{5,1}},$$

where $i_{5,1}$ is the first current value in the fifth pulse and $i_{5,8}$ is the last current value in the fifth pulse. The ratio of the normalized current value of the fourth pulse to the normalized current value of the fifth pulse may be represented by the equation $$\text{Ratio} = \frac{i_{4,8} * i_{5,1}}{i_{4,1} * i_{5,8}},$$

where $i_{4,1}$ is the first current value in the fourth pulse, $i_{4,8}$ is the last current value in the fourth pulse, $i_{5,1}$ is the first current value in the fifth pulse, and $i_{5,8}$ is the last current value in the fifth pulse.

The processor of the biosensor may measure the output signal. The processor may measure the output signal intermittently. The output signal may be responsive to a pulsed sequence. The output signal may be responsive to a gated amperometry electrochemical system.

BRIEF DESCRIPTION OF THE DRAWINGS

The invention may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

The present invention provides an abnormal output detection system for a biosensor. The abnormal output detection system improves the accuracy and precision of the biosensor in determining whether an output signal has a shape or configuration that may not provide an accurate and/or precise analysis of a biological fluid. The biosensor generates an output signal in response to a redox reaction of the analyte. The output signal may be measured and correlated to the concentration of an analyte in the biological fluid. The biosensor normalizes the output signal and compares the normalized output signal with one or more control limits. The biosensor generates an error signal when the normalized output signal is not within the control limits. The abnormal output detection system may be used separately or along with other error detection systems. The biosensor may be utilized to determine one or more analyte concentrations, such as glucose, uric acid, lactate, cholesterol, bilirubin, or the like, in a biological fluid, such as whole blood, urine, saliva, or the like.

Figure 1:
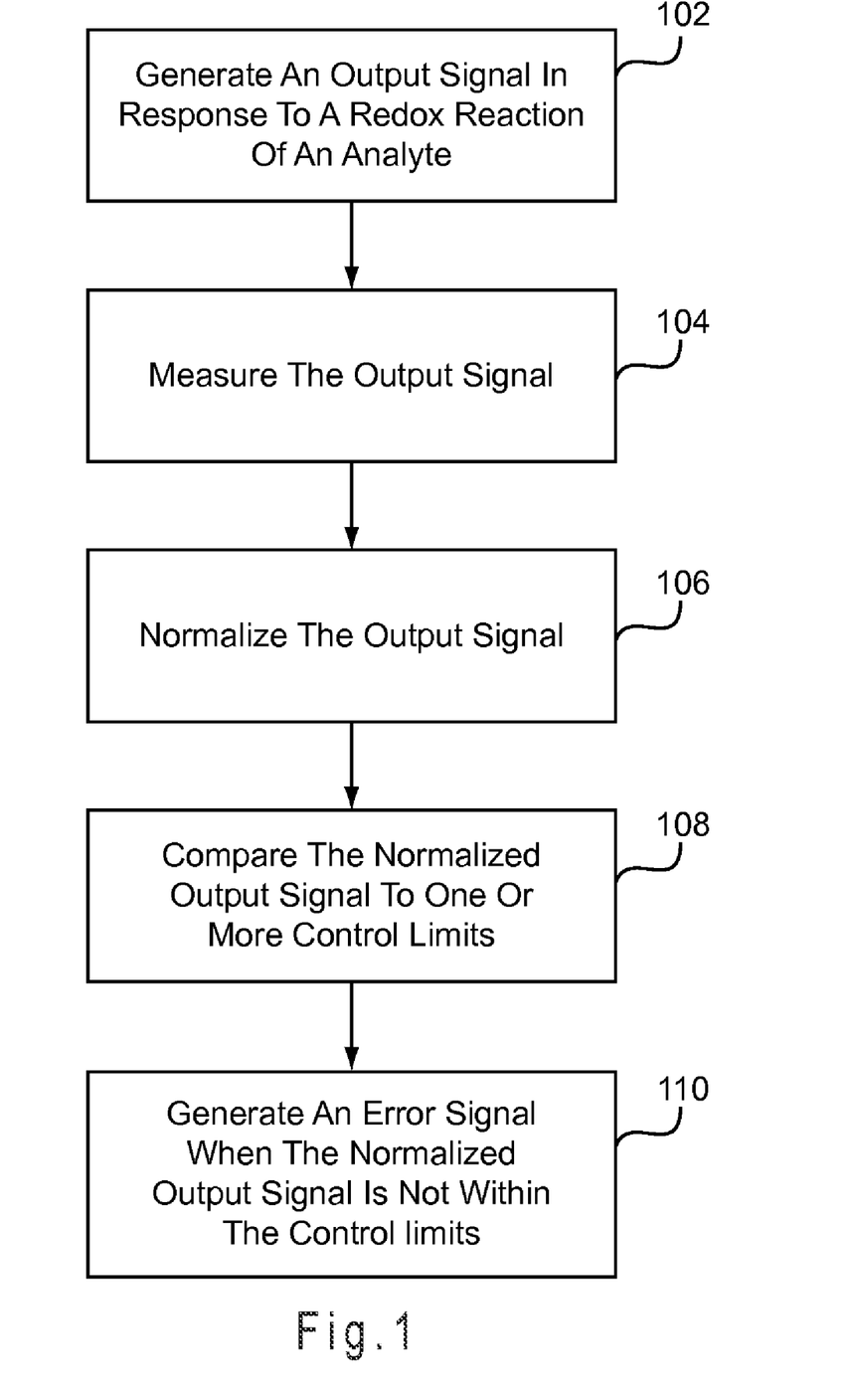
FIG. 1 represents a method for detecting an abnormal output signal in a biosensor.

FIG. 1 represents a method for detecting an abnormal output from a biosensor. A normal output signal has a shape or configuration that may provide an accurate and/or precise analysis of a biological fluid. An abnormal output signal has a shape or configuration that may not provide an accurate and/or precise analysis of a biological fluid. In 102, the biosensor generates an output signal in response to a redox reaction of an analyte in a sample of a biological fluid. In 104, the biosensor measures the output signal. In 106, the biosensor normalizes the output signal. In 108, the biosensor compares the normalized output signal to one or more control limits. In 110, the biosensor generates an error signal when a normalized output signal is not within the control limits.

In 102 of FIG. 1, the biosensor generates an output signal in response to an oxidation/reduction or redox reaction of an analyte in a sample of a biological fluid. The output signal may be generated using an optical sensor system, an electrochemical sensor system, or the like.

Optical sensor systems generally measure the amount of light absorbed or generated by the reaction of a chemical indicator with the analyte redox reaction. An enzyme may be included with the chemical indicator to enhance the reaction kinetics. The output signal or light from an optical system may be converted into an electrical signal such as current or potential.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

Electrochemical systems apply an input signal to the sample of the biological fluid. The input signal may be a potential or current and may be constant, variable, or a combination thereof such as when an AC signal is applied with a DC signal offset. The input signal may be applied as a single pulse or in multiple pulses, sequences, or cycles. The analyte undergoes a redox reaction when the input signal is applied to the sample. An enzyme or similar species may be used to enhance the redox reaction of the analyte. A mediator may be used to maintain the oxidation state of the enzyme. The redox reaction generates the output signal that may be measured constantly or periodically during transient and/or steady-state output. Various electrochemical processes may be used such as amperometry, coulometry, voltammetry, or the like. Gated amperometry and gated voltammetry also may be used.

In amperometry, a potential or voltage is applied to a sample of the biological fluid. The redox reaction of the analyte generates a current in response to the potential. The current is measured over time to quantify the analyte in the sample. Amperometry generally measures the rate at which the analyte is oxidized or reduced to determine the analyte concentration in the sample. Biosensor systems using amperometry are described in U.S. Pat. Nos. 5,620,579; 5,653,863; 6,153,069; and 6,413,411.

In coulometry, a potential is applied to a sample of the biological fluid to exhaustively oxidize or reduce the analyte within the sample. The potential generates a current that is integrated over the time of oxidation/reduction to produce an electrical charge representing the analyte concentration. Coulometry generally captures the total amount of analyte within the sample. A biosensor system using coulometry for whole blood glucose measurement is described in U.S. Pat. No. 6,120,676.

In voltammetry, a varying potential is applied to a sample of biological fluid. The redox reaction of the analyte generates current in response to the applied potential. The current is measured over time to quantify the analyte in the sample. Voltammetry generally measures the rate at which the analyte is oxidized or reduced to determine the analyte concentration in the sample. Additional information about voltammetry may be found in "Electrochemical Methods: Fundamentals and Applications" by A. J. Bard and L. R. Faulkner, 1980.

In gated amperometry and gated voltammetry, pulsed inputs are used as described in U.S. Provisional Patent Application Nos. 60/700,787, filed Jul. 20, 2005, and 60/722,584, filed Sep. 30, 2005, respectively, which are incorporated by reference.

Figure 2:
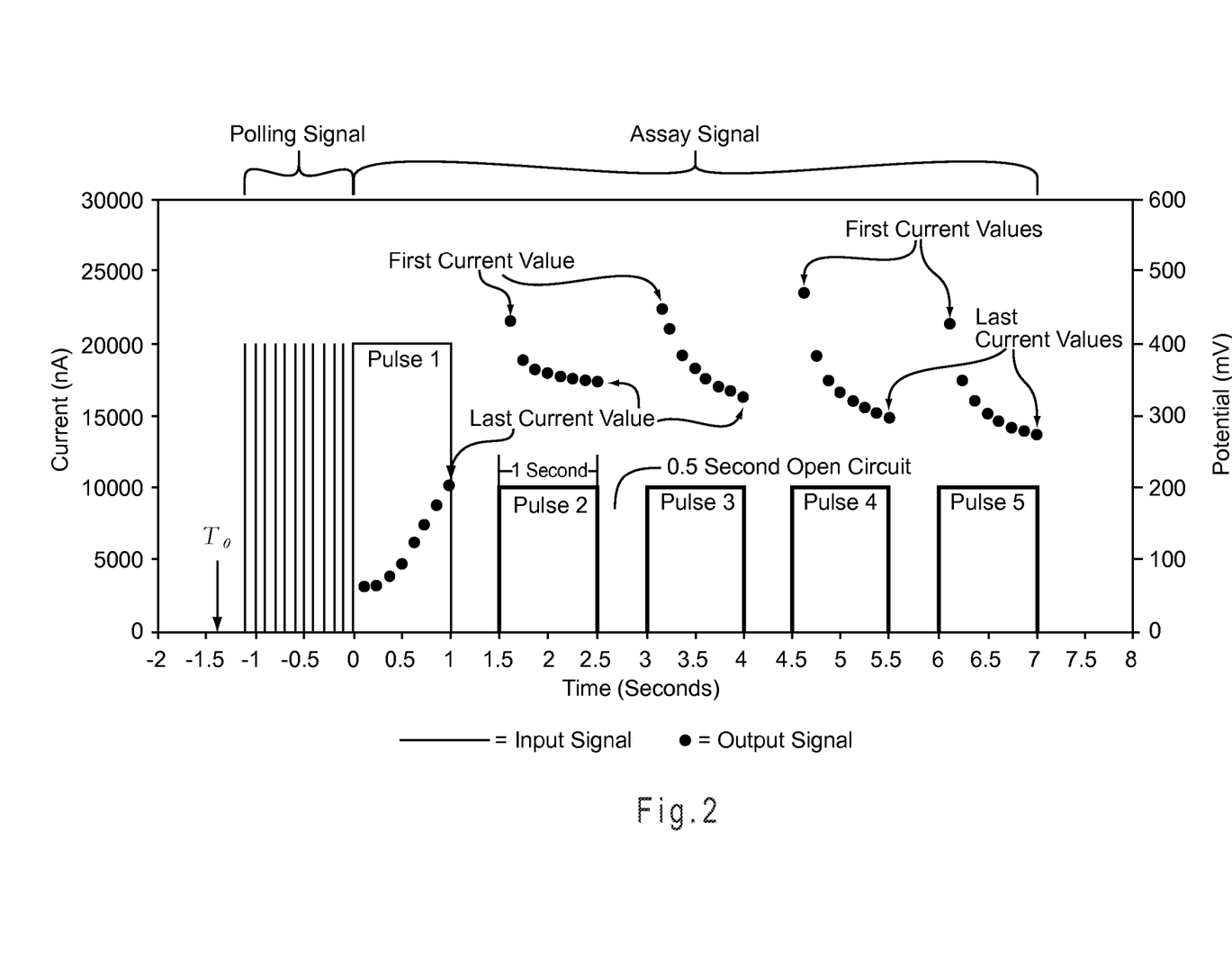
FIG. 2 is a graph illustrating the output signals in relation to the input signals for an electrochemical system using gated amperometry.

FIG. 2 is a graph illustrating the output signals in relation to the input signals for an electrochemical system using gated amperometry. The input signals are potentials applied to the sample of the biological fluid. The input signals include a polling input signal and an assay input signal. The output signals are currents generated from the sample. The output signals include a polling output signal and an assay output signal. The sample generates the assay output signal from the redox reaction of glucose in whole blood in response to the assay input signal. The input and output signals may be for a biosensor having working and counter electrodes. Other biosensors may be used including those with additional electrodes and different configurations. Other analyte concentrations may be measured including those in other biological fluids. Other output signals may be generated including those that decline initially and those that decline in all pulses.

The assay output signal in FIG. 2 has a normal shape or configuration. The current values in the first pulse increase from the first to the last current value. The current values in the second through the fifth pulses decrease or decay from the first to last current value in each pulse. An abnormal shape or configuration includes current values that increase in any of the second through the fifth pulses. An abnormal shape or configuration includes current values that decrease or decay too rapidly (a steeper slope) or too slowly (a flatter slope). Other abnormal shapes and configurations may occur.

In use, a sample of the biological fluid is deposited in the biosensor. The biosensor applies a polling signal to the sample from about −1.25 seconds through about 0 seconds. The pulses have a pulse width of about 5-10 ms and a pulse interval of about 125 ms. The biosensor generates a polling output signal in response to the polling input signal. The biosensor measures the polling output signal. The biosensor may have a potentiostat that provides the polling output signal to the input of an analog comparator.

When the polling output signal is equal to or greater than a polling threshold, the biosensor applies the assay input signal to the electrodes from about 0 seconds through about 7 seconds. The polling threshold valve may be about 250 nA. The comparator may compare the polling output signal to the polling threshold value. When the polling output signal exceeds the polling threshold value, the output signal of the comparator may trigger the launch of the assay input signal.

During the assay input signal, the biosensor applies a first pulse having a potential of about 400 mV for about 1 sec to the working and counter electrodes. The first pulse is followed by a 0.5 sec relaxation, which may be an essentially open circuit or the like. The assay output signal or current within the first pulse is measured and stored in a memory device. The biosensor may apply a second pulse to the working and counter electrodes at about 200 mV for about 1 sec. The assay output signal or current within the second pulse is measured and stored in a memory device. The biosensor continues applying pulses from the assay input signal to the working and counter electrodes until the end of the assay period or for as long as desired by the biosensor. The assay period may be about 7 seconds. The biosensor may measure and store assay output signal or current within each pulse.

The polling input signal is an electrical signal, such as current or potential, that pulses or turns on and off at a set frequency or interval. The sample generates a polling output signal in response to the polling input signal. The polling output signal is an electrical signal, such as current or potential. The biosensor may show the polling output signal on a display and/or may store the assay output signal in a memory device. The biosensor may apply the polling signal to detect when a sample connects with the electrodes. The biosensor may use other methods and devices to detect when a sample is available for analysis.

The polling input signal is a sequence of polling pulses separated by polling relaxations. During a polling pulse, the electrical signal is on. During a polling relaxation, the electrical signal is off. On may include time periods when an electrical signal is present. Off may include time periods when an electrical signal is not present. Off may not include time periods when an electrical signal is present but has essentially no amplitude. The electrical signal may switch between on and off by closing and opening an electrical circuit, respectively. The electrical circuit may be opened and closed mechanically, electrically, or the like.

A polling input signal may have one or more polling pulse intervals. A polling pulse interval is the sum of a polling pulse and a polling relaxation. Each polling pulse has an amplitude and a polling pulse width. The amplitude indicates the intensity of the potential, the current, or the like of the electrical signal. The amplitude may vary or be a constant during the polling pulse. The polling pulse width is the time duration of a polling pulse. The polling pulse widths in a polling input signal may vary or be essentially the same. Each polling relaxation has a polling relaxation width, which is the time duration of a polling relaxation. The polling relaxation widths in a polling input signal may vary or be essentially the same.

The polling input signal may have a polling pulse width of less than about 300 milliseconds (ms) and a polling pulse interval of less than about 1 sec. The polling input signal may have a polling pulse width of less than about 100 ms and a polling pulse interval of less than about 500 ms. The polling input signal may have a polling pulse width in the range of about 0.5 ms through about 75 ms and a polling pulse interval in the range of about 5 ms through about 300 ms. The polling input signal may have a polling pulse width in the range of about 1 ms through about 50 ms and a polling pulse interval in the range of about 10 ms through about 250 ms. The polling input signal may have a polling pulse width of about 5 ms and a polling pulse interval of about 125 ms. The polling input signal may have other pulse widths and pulse intervals.

The biosensor may apply the polling input signal to the sample during a polling period. The polling period may be less than about 15 minutes, 5 minutes, 2 minutes, or 1 minute. The polling period may be longer depending upon how a user uses the biosensor. The polling period may be in the range of about 0.5 second (sec) through about 15 minutes. The polling period may be in the range of about 5 sec through about 5 minutes. The polling period may be in the range of about 10 sec through about 2 minutes. The polling period may be in the range of about 20 sec through about 60 sec. The polling period may be in the range of about 30 through about 40 sec. The polling period may have less than about 200, 100, 50, or 25 pulse intervals. The polling period may have from about 2 through about 150 pulse intervals. The polling period may have from about 5 through about 50 pulse intervals. The polling period may have from about 5 through about 15 pulse intervals. The polling period may have about 10 pulse intervals. Other polling periods may be used.

The biosensor applies the assay input signal when the polling output signal is equal to or greater than a polling threshold. The polling threshold may be greater than about 5 percent (%) of the expected assay input signal at the beginning of the first pulse. The polling threshold may be greater than about 15% of the expected assay input signal at the beginning of the first pulse. The polling threshold may be in the range of about 5 percent (%) through about 50% of the expected assay input signal at the beginning of the first pulse.

Other polling thresholds may be used. The biosensor may indicate the polling output signal is equal to or greater than the polling threshold on a display.

The assay input signal is an electrical signal, such as current or potential, that pulses or turns on and off at a set frequency or interval. The sample generates an assay output signal in response to the assay input signal. The assay output signal is an electrical signal, such as current or potential.

The assay input signal is a sequence of assay pulses separated by assay relaxations. During an assay pulse, the electrical signal is on. During an assay relaxation, the electrical signal is off. On includes time periods when an electrical signal is present. Off includes time periods when an electrical signal is not present and does not include time periods when an electrical signal is present but has essentially no amplitude. The electrical signal switches between on and off by closing and opening an electrical circuit, respectively. The electrical circuit may be opened and closed mechanically, electrically, or the like.

An assay input signal may have one or more assay pulse intervals. An assay pulse interval is the sum of an assay pulse and an assay relaxation. Each assay pulse has an amplitude and an assay pulse width. The amplitude indicates the intensity of the potential, the current, or the like of the electrical signal. The amplitude may vary or be a constant during the assay pulse. The assay pulse width is the time duration of an assay pulse. The assay pulse widths in an assay input signal may vary or be essentially the same. Each assay relaxation has an assay relaxation width, which is the time duration of an assay relaxation. The assay relaxation widths in an assay input signal may vary or be essentially the same.

The assay input signal may have an assay pulse width of less than about 5 sec and an assay pulse interval of less than about 15 sec. The assay input signal may have an assay pulse width of less than about 3, 2, 1.5, or 1 sec and an assay pulse interval of less than about 13, 7, 4, 3, 2.5, or 1.5 sec. The assay input signal may have an assay pulse width in the range of about 0.1 sec through about 3 sec and an assay pulse interval in the range of about 0.2 sec through about 6 sec. The assay input signal may have an assay pulse width in the range of about 0.1 sec through about 2 sec and an assay pulse interval in the range of about 0.2 sec through about 4 sec. The assay input signal may have an assay pulse width in the range of about 0.1 sec through about 1.5 sec and an assay pulse interval in the range of about 0.2 sec through about 3.5 sec. The assay input signal may have an assay pulse width in the range of about 0.4 sec through about 1.2 sec and an assay pulse interval in the range of about 0.6 sec through about 3.7 sec. The assay input signal may have an assay pulse width in the range of about 0.5 sec through about 1.5 sec and an assay pulse interval in the range of about 0.75 sec through about 2.0 sec. The assay input signal may have an assay pulse width of about 1 sec and an assay pulse interval of about 1.5 sec. The assay input signal may have other pulse widths and pulse intervals.

The biosensor applies the assay input signal to the sample during an assay period. The assay period may have the same or a different duration than the polling period. The assay period of the assay input signal may be less than about 180, 120, 90, 60, 30, 15, 10, or 5 sec. The assay period may be in the range of about 1 sec through about 100 sec. The assay period may be in the range of about 1 sec through about 25 sec. The assay period may be in the range of about 1 sec through about 10 sec. The assay period may be in the range of about 2 sec through about 3 sec. The assay period may be about 2.5 sec. The assay period may have less than about 50, 25, 20, 15, 10, 8, 6, or 4 assay pulse intervals. The assay period may have assay pulse intervals in the range of about 2 through about 50. The assay period may have assay pulse intervals in the range of about 2 through about 25. The assay period may have assay pulse intervals in the range of about 2 through about 15. The assay period may have about 10 assay pulse intervals. Other assay periods may be used.

In 104 of FIG. 1, the biosensor measures the output signal generated by the redox reaction of the analyte in the sample. The biosensor may measure the output signal continuously or intermittently. For example, the biosensor measured the assay output signal intermittently during each pulse in FIG. 2, resulting in eight current values during each pulse. The sample generates the assay output signal in response to the redox reaction of the analyte in the biological fluid and the assay input signal. The biosensor may show the assay output signal on a display and/or may store assay output signal in a memory device. The biosensor may determine the concentration of the analyte in the sample from the output signal.

In 106 of FIG. 1, the biosensor normalizes the assay output signal. The normalized output signal may improve the comparison of assay output signals having different magnitudes due the amount of analyte in the sample of biological fluid. Generally, a larger amount of analyte in the sample generates a higher magnitude output signal than a smaller amount of analyte. The normalized output signal also may improve the mathematical evaluation of an output signal's shape or configuration to determine whether the output signal is normal or abnormal. The normalized output signal may permit the same control limits to be used on wider ranges of glucose and hematocrit levels.

To normalize the assay output signal, the biosensor determines the differences between one or more base output values and the measured output values of the assay output signal. The differences may be the arithmetic differences between the base and assay output values. The differences may be the ratios of the base and assay output signals. Other differences may be used. The base output values may be selected or predetermined from a statistical analysis of laboratory results. The base output values may be one or more of the measured output values of the assay output signal. A single base output value may be used for the assay output signal. Multiple base output values may be used such as a different base output value for each pulse in the assay output signal.

In a pulsed sequence such as gated amperometry or gated voltammetry, the assay output values may be normalized by dividing all the output values in a pulse by the first output value in the pulse. Other output values in each pulse may be the base output value. In a single pulse or similar sequence, the assay output values may be normalized by dividing all the output values in a pulse by the first or another output value. Other normalization methods may be used.

Table I shows the first and last current values for the pulses from the gate amperometry sequence of FIG. 2. The normalized current values are the ratios of the measured current values to the base current values. The base current values are the first current values in each pulse. The normalized current values show mathematically that the shape or configuration of the output signal increases from the first to the last current value in the first pulse. The normalized current values show mathematically that the shape or configuration of the output signal decreases from the first to the last current value in the first pulse.

TABLE I

| | Measured Current Value | Base Current Value | Normalized Current Value (Measured/Base) |
|---|---|---|---|
| Pulse 1, First Current Value ($i_{1,1}$) | 2,500 nA | 2,500 nA | 1.0 |
| Pulse 1, Last Current Value ($i_{1,8}$) | 10,000 nA | 2,500 nA | 4.0 |
| Pulse 2, First Current Value ($i_{2,1}$) | 21,000 nA | 21,000 nA | 1.0 |
| Pulse 2, Last Current Value ($i_{2,8}$) | 18,000 nA | 21,000 nA | 0.86 |
| Pulse 3, First Current Value ($i_{3,1}$) | 22,000 nA | 22,000 nA | 1.0 |
| Pulse 3, Last Current Value ($i_{3,8}$) | 17,000 nA | 22,000 nA | 0.77 |
| Pulse 4, First Current Value ($i_{4,1}$) | 24,000 nA | 24,000 nA | 1.0 |
| Pulse 4, Last Current Value ($i_{4,8}$) | 15,000 nA | 24,000 nA | 0.63 |
| Pulse 5, First Current Value ($i_{5,1}$) | 20,000 nA | 20,000 nA | 1.0 |
| Pulse 5, Last Current Value ($i_{5,8}$) | 14,000 nA | 20,000 nA | 0.70 |

In 108 of FIG. 1, the biosensor compares the normalized output signal with one or more control limits. The control limits are mathematical representations of thresholds where the shape or configuration of the output signal transitions from normal to abnormal. Control limits may be selected or predetermined for application to all or particular portions of the output signal. A particular portion of the output signal includes one or more pulses, one or more output values in each pulse or a particular pulse, and the like. Different control limits may be used for different portions of the output signal. Different control limits may be used for different ranges of glucose, hematocrit, and the like. Control limits may be selected or predetermined for application to the normalized output signal of a particular output signal value in a particular pulse. Control limits may be selected or predetermined for application to the mathematical relationship between output signal values in different pulses. The control limits may be selected to further define a desired shape or configuration of output signal. The control limits may be predetermined from a statistical or similar analysis of laboratory results. Other control limits may be used.

In the assay output signal of FIG. 2, control limits were selected or predetermined for the normalized current value of the last pulse in the fourth pulse ($R_4$), the normalized current value of the last pulse in the fifth pulse ($R_5$), and the ratio of $R_4$ to $R_5$ (Ratio). While control limits for the fourth and fifth pulses were used, other control limits could be used including those for the fourth and fifth pulses and those for other pulses in the assay output signal.

The normalized current value of the last pulse in the fourth pulse ($R_4$) may be represented by the following equation:

$$R_4 = \frac{i_{4,8}}{i_{4,1}} \quad (1)$$

Substituting the values from Table I into equation (1), yields:

$$R_4 = \frac{15,000 \text{ nA}}{24,000 \text{ nA}} = 0.63$$

The normalized current value of the last pulse in the fifth pulse ($R_5$), may be represented by the following equation:

$$R_5 = \frac{i_{5,8}}{i_{5,1}} \quad (2)$$

Substituting the values from Table I into equation (2), yields:

$$R_5 = \frac{14,000 \text{ nA}}{20,000 \text{ nA}} = 0.70$$

The ratio of the normalized current value of the last pulse in the fourth pulse ($R_4$) to the normalized current value of the last pulse in the fifth pulse ($R_5$), may be represented by the following equation:

$$\text{Ratio} = \frac{R_4}{R_5} = \frac{i_{4,8}/i_{4,1}}{i_{5,8}/i_{5,1}} \quad (3)$$

Simplifying equation (3), yields:

$$\text{Ratio} = \frac{i_{4,8} * i_{5,1}}{i_{4,1} \cdot i_{5,8}} \quad (4)$$

Substituting the values from Table I into equation (4), yields:

$$\text{Ratio} = \frac{15,000 \text{ nA} * 20,000 \text{ nA}}{24,000 \text{ nA} * 14,000 \text{ nA}} = 0.89$$

The control limits for $R_4$, $R_5$, and Ratio are shown in Table II. $R_4$, $R_5$, and Ratio are within the applicable control limits indicating the assay output signal of FIG. 2 has a normal shape or configuration. Other control limits may be used.

TABLE II

| | Description | Value |
|---|---|---|
| $R4_{min}$ | R4 minimum limit | 0.45 |
| $R4_{max}$ | R4 maximum limit | 0.85 |
| $R5_{min}$ | R5 minimum limit | 0.45 |
| $R5_{max}$ | R5 maximum limit | 0.85 |
| $\text{Ratio}_{min}$ | Ratio minimum limit | 0.75 |
| $\text{Ratio}_{max}$ | Ratio maximum limit | 1.25 |

The control limits were selected on the basis of normalized current readings from more than 9,000 blood samples. The blood samples each were introduced to newly prepared or aged sensor strips disposed in a measuring device. Current readings were obtained from the strips at sample temperatures from about 10° C. to about 40° C. The blood samples had glucose concentrations from about 10 mg/dL to about 600 mg/dL and hematocrit concentrations from about 20% to about 55%. The normalized current values from each analysis were separated into known good and bad values on the basis of the underlying current profile. The control limits were selected to include acceptable variation about the mean of the good values using standard statistical techniques.

In 110 of FIG. 1, the biosensor generates an error signal in response to a normalized output signal that is not within the control limits. The error signal may be shown on a display device and/or retained in a memory device. The biosensor may provide the error signal during or after the analysis of one or more analytes in the sample is performed. The biosensor may provide the error signal immediately after detection and may stop the analysis of the analyte. The biosensor may not provide the concentration of the analyte in response to the error signal.

Figure 3:
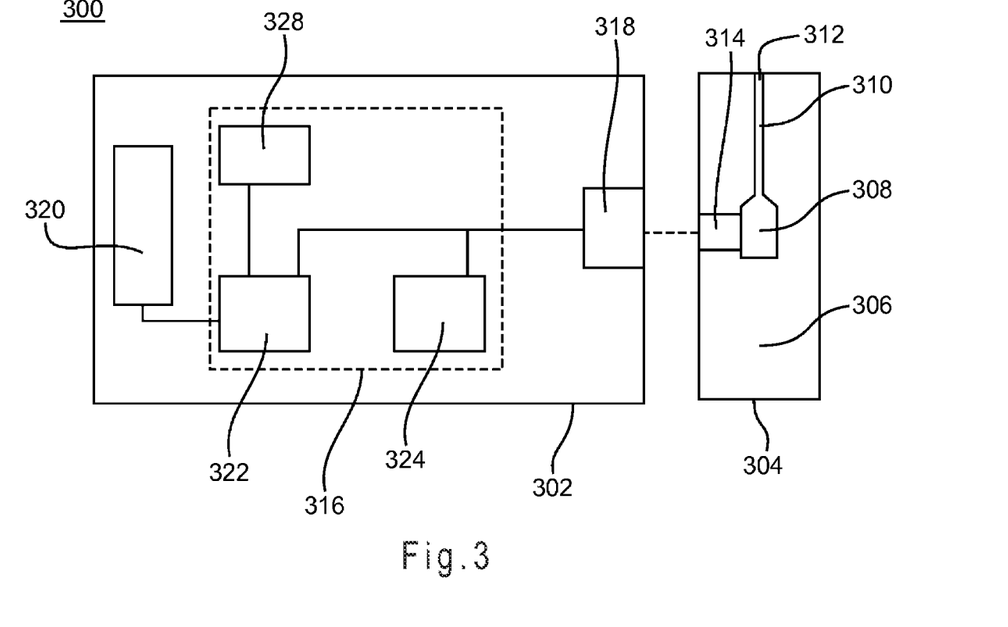
FIG. 3 depicts a schematic representation of a biosensor with an abnormal output signal detection system.

FIG. 3 depicts a schematic representation of a biosensor 300 with an abnormal output detection system. The biosensor 300 determines an analyte concentration in a sample of a biological fluid. The abnormal output detection system indicates when the shape or configuration of the output signal may provide an inaccurate and/or imprecise analysis of one or more analytes as previously discussed. The biosensor 300 includes a sensor strip 304 and a measuring device 302, which may be implemented as a bench-top device, a portable or hand-held device, or the like. The measuring device 302 and the sensor strip 304 may be adapted to implement an electrochemical sensor system, an optical sensor system, a combination thereof, or the like. The abnormal output detection system may improve the accuracy and/or precision of the biosensor 300 in determining when an abnormal output signal occurs. The biosensor 300 may be utilized to determine one or more analyte concentrations, such as glucose, uric acid, lactate, cholesterol, bilirubin, or the like, in a biological fluid, such as whole blood, urine, saliva, or the like. While a particular configuration is shown, the biosensor 300 may have other configurations, including those with additional components.

The sensor strip 304 has a base 306 that forms a reservoir 308 and a channel 310 with an opening 312. The reservoir 308 and channel 310 may be covered by a lid with a vent. The reservoir 308 defines a partially-enclosed volume (the cap-gap). The reservoir 308 may contain a composition that assists in retaining a liquid sample, such as water-swellable polymers or porous polymer matrices. Reagents may be deposited in the reservoir 308 and/or the channel 310. The reagents may include one or more enzymes, mediators, binders, and other active or non-reactive species. The reagents may include a chemical indicator for an optical system. The sensor strip 304 also may have a sample interface 314 disposed adjacent to the reservoir 308. The sample interface 314 may partially or completely surround the reservoir 308. The sensor strip 304 may have other configurations.

The sample interface 314 has conductors connected to a working electrode and a counter electrode. The electrodes may be substantially in the same plane. The electrodes may be separated by greater than 200 or 250 µm and may be separated from the lid by at least 100 µm. The electrodes may be disposed on a surface of the base 306 that forms the reservoir 308. The electrodes may extend or project into the cap-gap formed by the reservoir 308. A dielectric layer may partially cover the conductors and/or the electrodes. The sample interface 314 may have other electrodes and conductors. The sample interface 314 may have one or more optical portals or apertures for viewing the sample. The sample interface 314 may have other components and configurations.

The measuring device 302 includes electrical circuitry 316 connected to a sensor interface 318 and a display 320. The electrical circuitry 316 includes a processor 322 connected to a signal generator 324, and a storage medium 328. The measuring device may have other components and configurations.

The signal generator 324 provides electrical input signals to the sensor interface 318 in response to the processor 322. The electrical input signals may include the polling and assay input signals used in an electrochemical sensor system. The electrical input signals may include electrical signals used to operate or control a detector and light source in the sensor interface 318 for an optical sensor system. The electrical input signals may be transmitted by the sensor interface 318 to the sample interface 314. The electrical input signals may be a potential or current and may be constant, variable, or a combination thereof, such as when an AC signal is applied with a DC signal offset. The electrical input signals may be applied as a single pulse or in multiple pulses, sequences, or cycles. The signal generator 324 also may record signals received from the sensor interface 318 as a generator-recorder.

The storage medium 328 may be a magnetic, optical, or semiconductor memory, another computer readable storage device, or the like. The storage medium 328 may be a fixed memory device or a removable memory device such as a memory card.

The processor 322 implements the abnormal output detection, analyte analysis, and data treatment using computer readable software code and data stored in the storage medium 328. The processor 322 may start the abnormal output detection and analyte analysis in response to the presence of the sensor strip 304 at the sensor interface 318, the application of a sample to the sensor strip 304, user input, or the like. The processor 322 directs the signal generator 324 to provide the electrical input signals to the sensor interface 318.

The processor 322 receives and measures output signals from the sensor interface 318. The output signals may be electrical signals, such as current or potential, or light. The output signals may include polling and assay output signals. The output signals may include an assay output signal generated in response to the redox reaction of the analyte in the sample. The output signal may be generated using an optical system, an electrochemical system, or the like. The processor 322 may compare the polling output signals to one or more polling thresholds. The processor 322 may measure and correlate the assay output signal with the concentration of the analyte in the sample. The processor 322 may normalize the assay output signal and compare the normalized signal to one or more control limits as previously discussed.

The processor 322 provides an error signal of an abnormal output when the normalized output signal is not within the control limits, in other words, the shape or configuration of the assay output signal is not normal. The processor 322 may display the error signal on the display 320 and may store the error signal and related data in the storage medium 328. The processor 322 may provide the error signal at any time during or after the analyte analysis.

The processor 322 determines analyte concentrations from the assay output signals. The results of the analyte analysis are output to the display 320 and may be stored in the storage medium 328. Instructions regarding implementation of the analyte analysis may be provided by the computer readable software code stored in the storage medium 328. The code may be object code or any other code describing or controlling the described functionality. The data from the analyte analysis may be subjected to one or more data treatments, including the determination of decay rates, K constants, slopes, intercepts, and/or sample temperature in the processor 322.

The sensor interface 318 has contacts that connect or electrically communicate with the conductors in the sample interface 314 of the sensor strip 304. The sensor interface 318 transmits the electrical input signals from the signal generator 324 through the contacts to the connectors in the sample interface 314. The sensor interface 318 also transmits the output signals from the sample interface 314 to the processor 322 and/or signal generator 324. The sensor interface 308 also may include a detector, a light source, and other components used in an optical sensor system.

The display 320 may be analog or digital. The display may be an LCD display adapted to displaying a numerical reading. Other displays may be used.

In use, a liquid sample of a biological fluid is transferred into the cap-gap formed by the reservoir 308 by introducing the liquid to the opening 312. The liquid sample flows through channel 310 into reservoir 308, filling the cap-gap while expelling the previously contained air. The liquid sample chemically reacts with the reagents deposited in the channel 310 and/or reservoir 308.

The processor 322 detects when the sample of the biological fluid is available for analysis. The sensor strip 302 is disposed adjacent to the measuring device 302. Adjacent includes positions where the sample interface 314 is in electrical and/or optical communication with the sensor interface 308. Electrical communication includes the transfer of input and/or output signals between contacts in the sensor interface 318 and conductors in the sample interface 314. Optical communication includes the transfer of light between an optical portal in the sample interface 302 and a detector in the sensor interface 308. Optical communication also includes the transfer of light between an optical portal in the sample interface 302 and a light source in the sensor interface 308.

The processor 322 may direct the signal generator 324 to provide a polling input signal to sensor interface 318, which applies the polling input signal to the sample through the electrodes in the sample interface 314. The sample generates the polling output signal in response to the polling input signal. The sample interface 314 provides the polling output signal to the sensor interface 318. The processor 322 receives the polling output signal from the sensor interface 318. The processor 322 may show the polling output signal on the display 320 and/or may store the polling output signal in the storage medium 328.

The processor 322 may direct the signal generator 324 to provide the assay input signal to the sensor interface 318 when the polling output signal is equal to or greater than a polling threshold. The processor 322 may have comparator circuitry to provide the assay input signal to the sensor interface 318 when the polling output signal is equal to or greater than a polling threshold. In the comparator circuitry, the polling output signal is directed into the input of an electrical (analog) comparator or the like. The comparator compares the polling output signal with a polling threshold value. When the polling output signal is equal to or greater than the polling threshold value, the output of the comparator triggers the launch of the assay input signal.

The sensor interface 318 applies the assay input signal to the sample through the sample interface 314 during an assay period. The sample generates the assay output signal in response to the assay input signal. The sample interface 314 provides the assay output signal to the sensor interface 318.

The processor 322 receives the assay output signal from the sensor interface 318. The processor 322 measures the assay output signal generated by the sample. The processor 322 determines the analyte concentration of the sample in response to the assay output signal. The processor 322 may show the assay output signal on the display 320 and/or may store assay output signal in the storage medium 328. The processor 322 normalizes the assay output signal as previously discussed. The processor 322 compares the normalized output signal with one or more control limits during the assay period. The processor 322 provides an error signal of an abnormal output when the normalized output signal is not with the control limits. The error signal may be shown on the display 320 and/or retained in the storage medium 328. The processor 322 may provide the error signal immediately or another time, such as after the analyte analysis.

Without limiting the scope, application, or implementation, the methods and systems previously described may be implemented using the following algorithm:

Step 1: Turn on biosensor power
Step 2: Perform biosensor self-test
Step 3: Setup to poll for application of sample to sensor
  Set ASIC polling potential to $v_{poll}$
  Set ASIC threshold level to $i_{trigger}$
  Set polling periodic timer to expire at $int_{poll}$
Step 4: Setup for assaying the sensor current
  Wait for polling periodic timer to expire
  Enable ASIC charge pump
  Enable ASIC threshold detector ($i_{trigger}$)
  Enable polling potential ($v_{poll}$)
  Select sensor channel which applies potential to sensor
  Wait for settling time $t_{poll}$
Step 5: Test if the sensor current exceeds the threshold
Step 6: Delay and test sensor current again
Step 7: Upon detection of Sample Application
  start counting time
  launch pulse sequence
Step 8: Pulse 1 - Measure sensor currents $i_{1,1}$ and $i_{1,8}$
  Pulse 1 starts at time $t_{p1}$
  Set Pulse 1 duration to $d_{p1}$
  Set Pulse 1 sensor potential to $v_{p1}$
  Select sensor channel to apply potential to sensor
  At time $t_{1,1}$, measure sensor signal, save value as $AD_{S11}$
  At time $t_{1,8}$, measure sensor signal, save value as $AD_{S18}$
Step 9: Delay 1 - Re-standardize electronics
  Delay 1 starts at end of $AD_2$ reading, disconnect sensor channel
  Delay 1 ends at beginning of Pulse 2
  Set potential to $V_{standardize}$
  At time $t_{c1}$, select reference resistor channel then measure signal, save value as $AD_{R1}$
  At time $t_{c2}$, select offset channel then measure signal, save value as $AD_{O1}$
  Note: sensor currents starting at Pulse 1 are calculated from the $AD_{R1}$ and $AD_{O1}$ measurements
Step 10: Pulse 2 - Measure sensor currents $i_{2,1}$ and $i_{2,8}$
  Pulse 2 starts at time $t_{p2}$
  Set Pulse 2 duration to $d_{p2}$
  Set Pulse 2 sensor potential to $v_{p2}$
  Select sensor channel to apply potential to sensor
  At time $t_{2,1}$, measure sensor signal, save value as $AD_{S21}$
  At time $t_{2,8}$, measure sensor signal, save value as $AD_{S28}$
Step 11: Delay 2 -
  Delay 2 starts at end of $AD_{S3}$ reading, disconnect sensor channel
  Delay 2 ends at beginning of Pulse 3
  Select offset channel to disconnect sensor
Step 12: Pulse 3 - Measure sensor currents: $i_{3,1}$ and $i_{3,8}$
  Pulse 3 starts at time $t_{p3}$
  Set Pulse 3 duration to $d_{p3}$
  Set Pulse 3 sensor potential to $v_{p3}$
  Select sensor channel to apply potential to sensor
  At time $t_{3,1}$, measure sensor signal, save value as $AD_{S31}$
  At time $t_{3,8}$, measure sensor signal, save value as $AD_{S38}$
Step 13: Delay 3 - $T_1$ and $i_{wet}$
  Delay 3 starts at end of $AD_{S38}$ reading, disconnect sensor channel -continued Delay 3 ends at beginning of Pulse 4
Set potential to $V_{standardize}$
At time $t_{c3}$, select thermistor channel then measure signal, save value as $AD_{T1}$
At time $t_{wet}$, select offset channel then measure signal, save value as $AD_{wet}$ Step 14: Pulse 4 - Measure sensor currents: $i_{4,1}$, $i_{4,4}$, and $i_{4,8}$
Pulse 4 starts at time $t_{p4}$
Set Pulse 4 duration to $d_{p4}$
Set Pulse 4 sensor potential to $v_{p4}$
Select sensor channel to apply potential to sensor
At time $t_{4,1}$, measure sensor signal, save value as $AD_{S41}$
At time $t_{4,4}$, measure sensor signal, save value as $AD_{S44}$
At time $t_{4,8}$, measure sensor signal, save value as $AD_{S48}$ Step 15: Delay 4 -
Delay 4 starts at end of $AD_{S48}$ reading, disconnect sensor channel
Delay 4 ends at beginning of Pulse 5
Select offset channel to disconnect sensor Step 16: Pulse 5 - Measure sensor currents: $i_{5,1}$, $i_{5,4}$, and $i_{5,8}$
Pulse 5 starts at time $t_{p5}$
Set Pulse 5 duration to $d_{p5}$
Set Pulse 5 sensor potential to $v_{p5}$
Select sensor channel to apply potential to sensor
At time $t_{5,1}$, measure sensor signal, save value as $AD_{S51}$
At time $t_{5,4}$ measure sensor signal, save value as $AD_{S54}$
At time $t_{5,8}$, measure sensor signal, save value as $AD_{S58}$
Disable ASIC analog functions Step 17: Compute ratios $$\text{Compute } R_4 = \frac{i_{4,8}}{i_{4,1}}$$

$$\text{Compute } R_5 = \frac{i_{5,8}}{i_{5,1}}$$

$$\text{Compute Ratio} = \frac{i_{4,8} * i_{5,1}}{i_{4,1} * i_{5,8}}$$

Step 18: Look up slope and intercept for lot calibration number
S = Slope value for current lot calibration number
Int = Intercept value for current lot calibration number
Step 19: Adjust slope and intercept for temperature effect
Step 20: Calculate glucose concentration at 25° C.
Step 21: Convert to target reference (plasma vs. WB reference)
Step 22: Check underfill
Step 23: Check ratios for "Abnormal Behavior"
If ($R_4 > R4_{max}$ or
$R_4 < R4_{min}$ or
$R_5 > R5_{max}$ or
$R_5 < R5_{min}$ or
Ratio > $Ratio_{max}$ or
Ratio < $Ratio_{min}$) then
BEGIN
If (ErrorCode is not set) then set ErrorCode to "Abnormal Behavior"
END
Step 24: If low glucose, check ratios again for "Abnormal Behavior"
If ($G_{25C} < G_{lim}$) then
BEGIN
If ($R_4 > R4L_{max}$ or
$R_4 < R4L_{min}$ or
$R_5 > R5L_{max}$ or
$R_5 < R5L_{min}$ or
Ratio > $RatioL_{max}$ or
Ratio < $RatioL_{min}$) then
BEGIN
If (ErrorCode is not set) then set ErrorCode to "Abnormal Behavior"
END
Step 25: Check for extreme glucose levels
Step 26: Display result The algorithm may have other subroutines including those to check for errors such as sample temperature and underfill conditions. The constants that may be used in the algorithm are given in Table III and Table IV below. Other constants may be used.

TABLE III

| Constant | Description | Value | Units |
|---|---|---|---|
| $v_{poll}$ | polling voltage | 400 | mV |
| $int_{poll}$ | polling interval | 125 | ms |
| $t_{poll}$ | polling duration | 10 | minutes |
| $i_{trigger}$ | threshold detect trigger current | 250 | nA |
| $t_{p1}$ | pulse 1 start time | 0 | sec |
| $d_{p1}$ | pulse 1 duration | 1 | second |
| $v_{p1}$ | pulse 1 voltage level | 400 | mV |
| $t_{1,1}$ | time of sensor current reading 1 (7-sec only) | 0.125 | sec |
| $t_{1,8}$ | time of sensor current reading 2 | 1.00 | sec |
| $t_{c1}$ | Offset reading time | 1.125 | sec |
| $t_{c2}$ | Reference reading time | 1.25 | sec |
| $t_{p2}$ | pulse 2 start time | 1.5 | sec |
| $d_{p2}$ | pulse 2 duration | 1 | second |
| $v_{p2}$ | pulse 2 voltage level | 200 | mV |
| $t_{2,1}$ | time of sensor current reading 3 | 1.625 | sec |
| $t_{2,8}$ | time of sensor current reading 4 | 2.50 | sec |
| $t_{p3}$ | pulse 3 start time (7-sec only) | 3 | sec |
| $d_{p3}$ | pulse 3 duration (7-sec only) | 1 | second |
| $v_{p3}$ | pulse 3 voltage level (7-sec only) | 200 | mV |
| $t_{3,1}$ | time of sensor current reading 5 (7-sec only) | 3.125 | sec |
| $t_{3,8}$ | time of sensor current reading 6 (7-sec only) | 4.00 | sec |
| $t_{c3}$ | Thermistor reading time | 4.125 | sec |
| $t_{wet}$ | Time of wet sensor current reading | 4.25 | sec |
| $t_{p4}$ | pulse 4 start time (7-sec only) | 4.5 | second |
| $d_{p4}$ | pulse 4 duration (7-sec only) | 1 | second |
| $v_{p4}$ | pulse 4 voltage level (7-sec only) | 200 | mV |
| $t_{4,1}$ | time of sensor current reading 7 (7-sec only) | 4.625 | sec |
| $t_{4,4}$ | time of sensor current reading 8 (7-sec only) | 5.00 | sec |
| $t_{4,8}$ | time of sensor current reading 9 (7-sec only) | 5.50 | sec |
| $t_{p5}$ | pulse 5 start time (7-sec only) | 6 | sec |
| $d_{p5}$ | pulse 5 duration (7-sec only) | 1 | second |
| $v_{p5}$ | pulse 5 voltage level (7-sec only) | 200 | mV |
| $t_{5,1}$ | time of sensor current reading 10 (7-sec only) | 6.125 | sec |
| $t_{5,4}$ | time of sensor current reading 11 (7-sec only) | 6.50 | sec |
| $t_{5,8}$ | time of sensor current reading 12 (7-sec only) | 7.00 | sec |

TABLE IV

| Constant | Description | Value | Units |
|---|---|---|---|
| $R4_{min}$ | R4 minimum limit | 0.45 | — |
| $R4_{max}$ | R4 maximum limit | 0.85 | — |
| $R5_{min}$ | R5 minimum limit | 0.45 | — |
| $R5_{max}$ | R5 maximum limit | 0.85 | — |
| $Ratio_{min}$ | Ratio minimum limit | 0.75 | — |
| $Ratio_{max}$ | Ratio maximum limit | 1.25 | — |
| $G_{lim}$ | Glucose limit for different R4, R5 and R4/R5 values | 50 | mg/dL |
| $R4L_{min}$ | R4 minimum limit for G25 less than Glim | 0.45 | — |
| $R4L_{max}$ | R4 maximum limit for G25 less than Glim | 0.85 | — |
| $R5L_{min}$ | R5 minimum limit for G25 less than Glim | 0.45 | — |
| $R5L_{max}$ | R5 maximum limit for G25 less than Glim | 0.85 | — |
| $RatioL_{min}$ | Ratio minimum limit for G25 less than Glim | 0.75 | — |
| $RatioL_{max}$ | Ratio maximum limit for G25 less than Glim | 1.25 | — |

To provide a clear and more consistent understanding of the specification and claims of this application, the following definitions are provided.

"Analyte" is defined as one or more substances present in a sample. An analysis determines the presence and/or concentration of the analyte present in the sample.

"Sample" is defined as a composition that may contain an unknown amount of the analyte. Typically, a sample for electrochemical analysis is in liquid form, and preferably the sample is an aqueous mixture. A sample may be a biological sample, such as blood, urine, or saliva. A sample also may be a derivative of a biological sample, such as an extract, a dilution, a filtrate, or a reconstituted precipitate.

"Conductor" is defined as an electrically conductive substance that remains stationary during an electrochemical analysis.

"Accuracy" is defined as how close the amount of analyte measured by a sensor system corresponds to the true amount of analyte in the sample. Accuracy may be expressed in terms of the bias of the sensor system's analyte reading in comparison to a reference analyte reading. Larger bias values reflect less accuracy.

"Precision" is defined as how close multiple analyte measurements are for the same sample. Precision may be expressed in terms of the spread or variance among multiple measurements.

"Redox reaction" is defined as a chemical reaction between two species involving the transfer of at least one electron from a first species to a second species. Thus, a redox reaction includes an oxidation and a reduction. The oxidation half-cell of the reaction involves the loss of at least one electron by the first species, while the reduction half-cell involves the addition of at least one electron to the second species. The ionic charge of a species that is oxidized is made more positive by an amount equal to the number of electrons removed. Likewise, the ionic charge of a species that is reduced is made less positive by an amount equal to the number of electrons gained.

"Mediator" is defined as a substance that may be oxidized or reduced and that may transfer one or more electrons. A mediator is a reagent in an electrochemical analysis and is not the analyte of interest, but provides for the indirect measurement of the analyte. In a simple system, the mediator undergoes a redox reaction in response to the oxidation or reduction of the analyte. The oxidized or reduced mediator then undergoes the opposite reaction at the working electrode of the sensor strip and is regenerated to its original oxidation number.

"Binder" is defined as a material that provides physical support and containment to the reagents while having chemical compatibility with the reagents.

"Underfill condition" is defined as a sample of biological fluid in a biosensor having a size or volume that is not large enough for the biosensor to accurately and/or precisely analyze the concentration of one or more analytes in the biological fluid.

"Handheld device" is defined as a device that may be held in a human hand and is portable. An example of a handheld device is the measuring device accompanying ASCENSIA® Elite Blood Glucose Monitoring System, available from Bayer HealthCare, LLC, Elkhart, Ind.

While various embodiments of the invention have been described, it will be apparent to those of ordinary skill in the art that other embodiments and implementations are possible within the scope of the invention.

The invention claimed is:

1. A method for increasing biosensor precision and/or accuracy, comprising:
applying a pulsed input signal to a sample of a biological fluid, the pulses of the input signal separated by relaxations where the electrical signal is off;
generating an output signal from a redox reaction of an analyte in the sample, where the output signal is responsive to the pulses of the input signal;
measuring the output signal from the redox reaction of the analyte in the sample;
normalizing the output signal from the redox reaction of the analyte in the sample, where the output signal is responsive to an analyte concentration in the sample;
comparing the normalized output signal from at least two of the pulses separated by relaxations to at least one control limit, where the at least one control limit represents an acceptable variation of the normalized output signal; and
generating an error signal when the normalized output signal is not within the at least one control limit.

2. The method of claim 1, where the normalizing includes determining a difference between at least one base output value and at least two measured output values of the output signal, where the at least one base output value is used in the normalizing of the at least two measured output values.

3. The method of claim 2, where the input signal includes a gated amperometric input signal including pulses and the output signal is responsive to the pulses of the gated amperometric input signal.

4. The method of claim 3, where the gated amperometric input signal comprises at least five pulses.

5. The method of claim 4, where the normalized current value of the fourth pulse, $R_4$, is represented by the following equation:

$$R_4 = \frac{i_{4,8}}{i_{4,1}},$$

where $i_{4,1}$ is the first current value in the fourth pulse and $i_{4,8}$ is the last current value in the fourth pulse.

6. The method of claim 5, where $R_4$ is greater than or equal to 0.45, and where $R_4$ is less than or equal to 0.85.

7. The method of claim 4, where the normalized current value of the fifth pulse, $R_5$, is represented by the following equation:

$$R_5 = \frac{i_{5,8}}{i_{5,1}},$$

where $i_{5,1}$ is the first current value in the fifth pulse and $i_{5,8}$ is the last current value in the fifth pulse.

8. The method of claim 7, where $R_5$ is greater than or equal to 0.45, and where $R_5$ is less than or equal to 0.85.

9. The method of claim 4, where the ratio of the normalized current value of the fourth pulse to the normalized current value of the fifth pulse is represented by the following equation:

$$\text{Ratio} = \frac{i_{4,8} * i_{5,1}}{i_{4,1} * i_{5,8}},$$

where $i_{4,1}$ is the first current value in the fourth pulse, $i_{4,8}$ is the last current value in the fourth pulse, $i_{5,1}$ is the first current value in the fifth pulse, and $i_{5,8}$ is the last current value in the fifth pulse.

10. The method of claim 9, where Ratio is greater than or equal to 0.75, and where Ratio is less than or equal to 1.25.

11. The method of claim 2, where the at least one base output value is a different measured output value of the output signal than at least one of the at least two measured output values.

12. The method of claim 1, where the normalizing includes dividing at least one output value of the output signal by a first output value from a pulse of the output signal.

13. The method of claim 1, where the sample of the biological fluid is whole blood, further comprising:
    separating normalized current values of the output signal in response to underlying current profiles; and
    selecting the at least one control limit to include an acceptable variation of the normalized current values about a mean using statistical techniques.

14. The method of claim 1, where a normalized output signal within the at least one control limit provides an accurate and/or precise analysis of the biological fluid and where a normalized output signal not within the at least one control limit does not provide an accurate and/or precise analysis of the sample of the biological fluid.

15. The method of claim 1, further comprising determining the at least one control limit from a statistical analysis of laboratory results.

16. The method of claim 1, further comprising detecting when the sample connects at least two electrodes with a polling input signal, where the input signal comprises the polling input signal and an assay input signal.

17. The method of claim 16, where the polling input signal has a polling pulse width of less than about 300 ms, and where the polling input signal has a polling pulse interval of less than about 1 sec.

18. The method of claim 17, where the polling input signal has a polling pulse width in the range of about 0.5 ms through about 75 ms, and where the polling input signal has a polling pulse interval in the range of about 5 ms through about 300 ms.

19. The method of claim 16, where the assay input signal has an assay pulse width of less than about 5 sec, and where the assay input signal has an assay pulse interval of less than about 15 sec.

20. The method of claim 19, where the assay input signal has an assay pulse width in the range of about 0.1 sec through about 3 sec, and where the assay input signal has an assay pulse interval in the range of about 0.2 sec through about 6 sec.

21. The method of claim 16, further comprising:
    applying the polling input signal during a polling period, where the polling period is less than about 180 sec; and
    applying the assay input signal during an assay period, where the assay period is less than about 180 sec.

22. The method of claim 16, further comprising:
    applying the polling input signal during a polling period, where the polling period is in the range of about 0.1 sec through about 10 sec; and
    applying the assay input signal during an assay period, where the assay period is in the range of about 1 sec through about 100 sec.

23. The method of claim 16, further comprising:
    applying a polling input signal to the sample for about 1.25 sec where the polling input signal has a polling pulse width of about 5-10 ms and a polling pulse interval of about 125 ms; and
    applying an assay input signal to the sample for about 7 sec, where the assay input signal has an assay pulse width of about 1 sec and an assay pulse interval of about 1.5 sec.

24. The method of claim 23, where the polling input signal has a potential of about 400 mV, where the assay input signal has a first pulse with a potential of about 400 mV, where the assay input signal has at least one other pulse with a potential of about 200 mV.

25. The method of claim 16, further comprising applying the assay input signal when a polling output signal is greater than or equal to a polling threshold.

26. The method of claim 25, where the polling threshold is about 250 nA.

27. The method of claim 1, where the measuring the output signal comprises measuring the output signal intermittently.

28. The method of claim 27, where the measuring the output signal intermittently comprises measuring at least eight current values in at least one pulse of the output signal.

* * * * *